US008623668B2

(12) United States Patent
Wirix-Speetjens et al.

(10) Patent No.: US 8,623,668 B2
(45) Date of Patent: Jan. 7, 2014

(54) METHOD FOR TRANSPORT OF MAGNETIC PARTICLES AND DEVICES THEREFOR

(75) Inventors: Roel Wirix-Speetjens, Maaseik (BE); William Fyen, Korbeek-Lo (BE); Gunter Reekmans, Zichem (BE)

(73) Assignee: IMEC, Leuven (BE)

( * ) Notice: Subject to any disclaimer, the term of this patent is extended or adjusted under 35 U.S.C. 154(b) by 1300 days.

(21) Appl. No.: 11/718,681

(22) PCT Filed: Nov. 7, 2005

(86) PCT No.: PCT/BE2005/000156
§ 371 (c)(1),
(2), (4) Date: Feb. 17, 2009

(87) PCT Pub. No.: WO2006/047840
PCT Pub. Date: May 11, 2006

(65) Prior Publication Data
US 2009/0170065 A1    Jul. 2, 2009

Related U.S. Application Data

(60) Provisional application No. 60/625,230, filed on Nov. 5, 2004.

(30) Foreign Application Priority Data

Apr. 22, 2005   (EP) ..................................... 05447090

(51) Int. Cl.
*G01N 33/553* (2006.01)
*G01N 33/53* (2006.01)

(52) U.S. Cl.
USPC .......................................... 436/526; 436/518

(58) Field of Classification Search
USPC .................................................. 436/526, 518
See application file for complete search history.

(56) References Cited

U.S. PATENT DOCUMENTS

| 4,395,746 | A | * | 7/1983 | Tanaka et al. | ................. | 361/143 |
| 5,981,297 | A | * | 11/1999 | Baselt | ............................ | 436/514 |
| 2002/0166760 | A1 | * | 11/2002 | Prentiss et al. | ................ | 204/155 |
| 2002/0166800 | A1 | | 11/2002 | Prentiss et al. | | |
| 2004/0018611 | A1 | | 1/2004 | Ward et al. | | |
| 2004/0023273 | A1 | * | 2/2004 | Puget et al. | ........................ | 435/6 |

FOREIGN PATENT DOCUMENTS

| EP | 1 462 173 | A1 | 9/2004 |
| EP | 1 462 174 | A1 | 9/2004 |
| EP | 1 469 311 | A1 | 10/2004 |
| WO | WO 01/96857 | A2 | 12/2001 |
| WO | WO 01/96857 | A3 | 12/2001 |
| WO | WO 03/046511 | A2 | 6/2003 |
| WO | WO 2005/010542 | A2 | 2/2005 |

OTHER PUBLICATIONS

European Search Report EP 05 44 7090 dated Jul. 18, 2005.

(Continued)

*Primary Examiner* — Mark Shibuya
*Assistant Examiner* — Pensee Do
(74) *Attorney, Agent, or Firm* — Knobbe Martens Olson & Bear LLP

(57) ABSTRACT

The present invention is related to a method for re-enabling transport by means of a magnetic field gradient transport mechanism of magnetic beads comprising a ligand in a solution on top of a surface comprising a receptor bound with said ligand, comprising the step of changing the properties of said solution such that dissociation occurs between said ligand and said receptor, and such that a sufficient repulsive interaction is created between said surface and said bead to allow transport of said bead.

29 Claims, 6 Drawing Sheets

(a)

(b)

(56) References Cited

OTHER PUBLICATIONS

Figure 1:
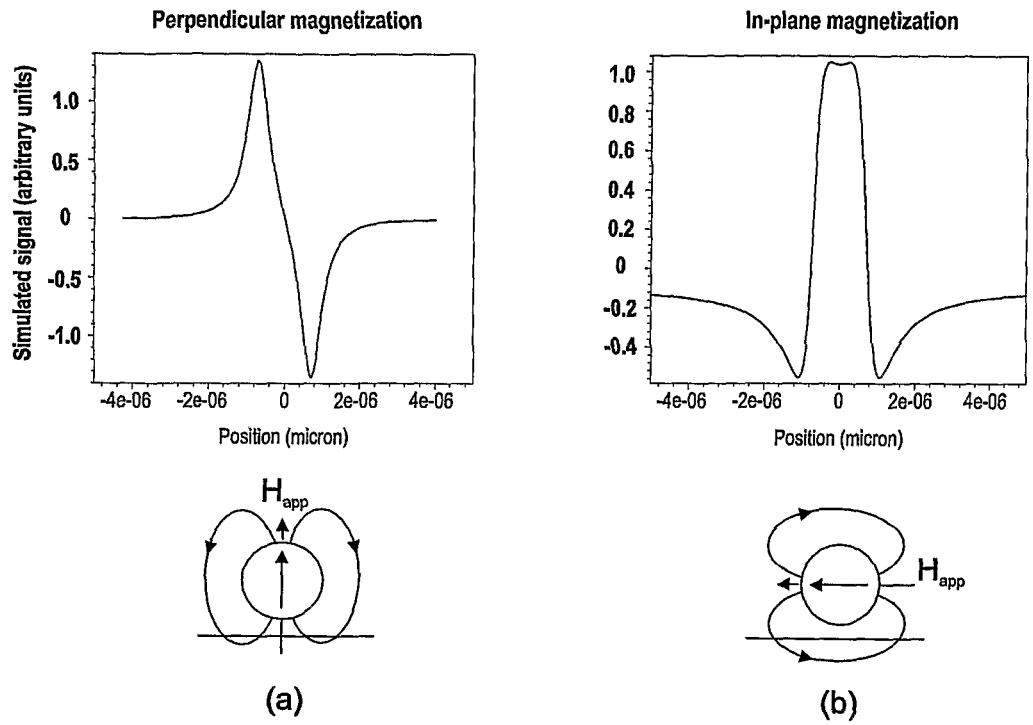

International Search Report for PCT/BE2004/000156, Feb. 21, 2006.
Whitesides, et al., "Manipulation of magnetic microbeads in suspension using micromagnetic systems fabricated with soft lithography," *Applied Physics Letters,* Mar. 19, 2001, 78/12, 1775-1777.
Rife, et al., "Design and performance of GMR sensors for the detection of magnetic microbeads in biosensors," *Sensors and Actuators,* 2003, A/107, 209-218.

* cited by examiner

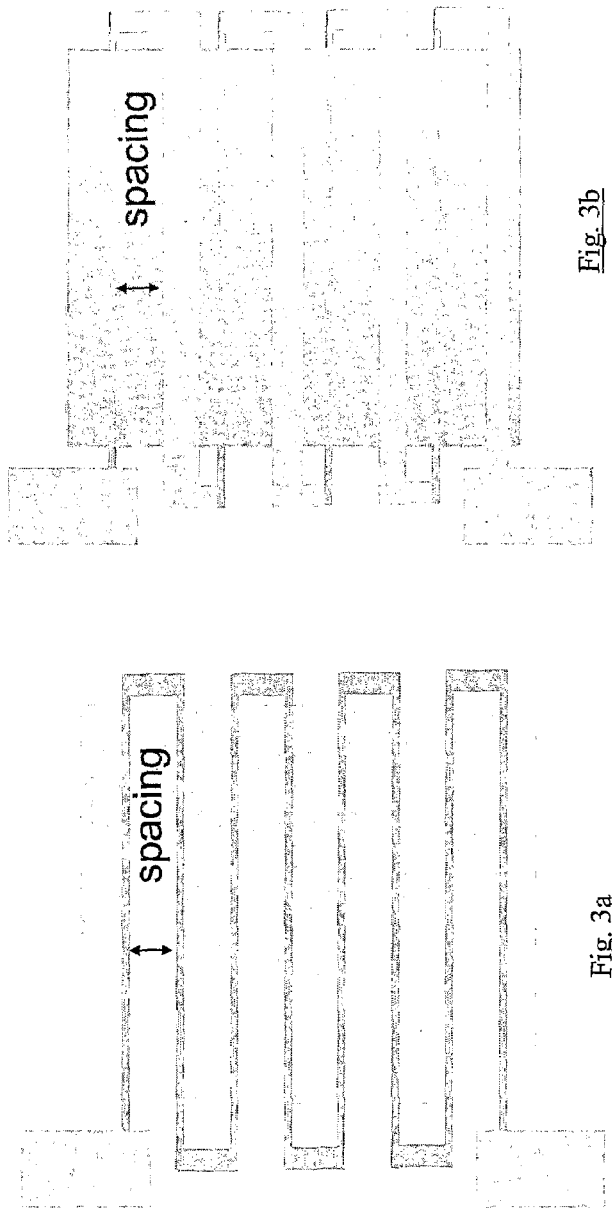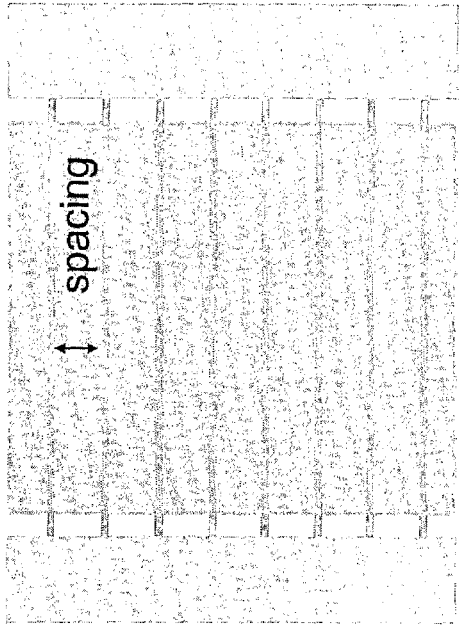
Fig. 3a
Fig. 3b
Fig. 3c

METHOD FOR TRANSPORT OF MAGNETIC PARTICLES AND DEVICES THEREFOR

FIELD OF THE INVENTION

The present invention is related to the field of microelectronic devices, designed to transport and manipulate magnetic beads, typically on chip. Some application domains are biochips and biosensors, used for molecular, in-vitro and point-of-care diagnostics in general; for the diagnosis of cancer, infectious diseases, auto-immune disorders, cardiovascular risk and neurodegenerative diseases, the detection of hormones, cytokines and acute phase reactants in particular; and for analysis in areas such as food quality and safety, animal diseases, environmental screening, etc. diagnostics, genetics and molecular studies.

STATE OF THE ART

Following the publication of the first draft of the human genome sequence, the next major task is to determine the function that each of the genes (i.e. >35,000) have in each of the tissues in the body over a range of environmental conditions. Using arrays of thousands of probes which are specific to individual genes, DNA microarrays enable the extent to which individual genes are switched on or off to be determined. Genetic variation among individuals also contributes to variation in the way genes behave in response to changes in the environment. Simultaneous detection of variation at thousands of locations (i.e. single nucleotide polymorphisms or SNPs) in the genome can also be achieved using DNA microarray technology. Applications of DNA microarrays therefore include gene expression profiling, gene sequencing, gene discovery, and genotyping, for users in healthcare, academia and the pharmaceutical and biotechnology industries. Currently the major factors limiting the uptake of DNA microarray technology include low sensitivity, the high cost of the technology, requirement for specialist operators and throughput. The same drawbacks are encountered in the development and use of technologies for the detection of proteins, cells and other biological species.

Electronic biochips have the potential to overcome these limitations. Here, exploitation of state-of-the-art micro- and nano-technology design, fabrication and characterization tools and processes enable development of devices and systems that can interface directly with biological reactions. A possibility involves combining magnetic bead-based bioassays with magnetic sensor technology. From a biotechnology perspective, superparamagnetic beads (e.g. 0.05-10.0 µm diameter) are available commercially from a number of sources with a range of surface functional chemistries, for well established applications including isolation and transportation of nucleic acids, proteins and whole cells. In microelectronics, GMR-based magnetic sensors have provided an enabling technology for memory applications.

Paramagnetic materials are materials that develop a magnetic moment parallel to any applied field. It contains microscopic permanent moments, like a ferromagnet, but the difference is they are only weakly interacting so that no long-ranged order can develop.

Thus, integration of superparamagnetic bead-based nucleic acid, protein and/or cellular assays on a functional biochip surface incorporating magnetic sensors, provides the basis for a range of biochip platforms.

Research groups now start to explore the unique ability of manipulating these particles by applying controlled magnetic forces. By immobilising biomolecules onto the particle's surface, a number of additional functionalities emerge, such as transfer of biomolecules to a specific location on the chip and testing or speeding up biomolecular recognition events. This turns the label, which used to be solely a means of detection, into a 'smart' label.

Today, all particle detection principles are based on a static detection. In a static detection, highly sensitive magnetic field sensors measure the magnetic field emanating from magnetic particles immobilised onto the surface and in the vicinity of the sensor. Given that the field generated by the particles diminishes very fast ($1/r^3$) and that these particles are immobilised at different distances from the sensor, each particle will contribute with a different magnitude to the total signal. This effect can lead to large deviations on the total signal but will disappear when many particles are detected (different contributions will average out, lowering the average signal per particle), but for low analyte concentration, this may be a problem.

Next to the detection of the magnetic beads, the problem of transport and manipulation of beads is a limiting factor, which has to be taken into account in biochip designs and methods.

In Whitesides et al., "Manipulation of magnetic microbeads in suspension using micromagnetic systems fabricated with soft lithography", Applied Physics Letters [Vol 78, Nr 12 Mar. 19th 2001, pages 1775-1777] and US2002/0166800, systems are described comprising current carrying wires that can generate strong local magnetic field gradients, which in their turn can control the position of magnetic microbeads in aqueous suspension.

In patent application EP1462173 another method for controlled transport of magnetic beads is disclosed. It concerns a method and corresponding devices for controlled transport of magnetic beads between a position X and different position Y, wherein said magnetic beads are manipulated or transported by applying successively a series of N local magnetic fields which have magnetic field gradients different from 0 in the neighbourhood of said magnetic beads is disclosed. Each of these N local magnetic fields is generated by a single current carrying structure, in which the current density is not constant. The state of the art demonstrated movement of magnetic particles that are suspended in essentially pure water (pH 7, ionic strength 1E-7 M).

Biomolecular bonds such as protein-protein protein-cell, nucleic acid—nucleic acid, etc. interactions are usually reversible and can be influenced in different ways, such as temperature, pH, solvent and other molecules or ions present. Regeneration of biomolecular recognition events using low/high pH, etc (see above) is known in biotechnology.

DLVO (Derjaguin-Landau-Verwey-Overbeek) theory explains absorption of particles onto substrates in aqueous solutions with a known pH value and ionic strength using electrostatic and van der waals interactions.

However, these parameters have an effect on the substrate charge and bead surface charge and therefor influence the DLVO interactions and the particle mobility associated to it. At present, changing such parameters has been avoided in order to avoid interference with the magnetic transport.

SUMMARY OF THE INVENTION

The present invention relates to a method for measuring the presence and/or concentration of magnetic particles by means of a sensor device.

A method of the invention comprises the steps of:
providing the surface of a sensor device with a solution containing said magnetic particles, subjecting said magnetic particles to an external magnetic field, applying a current through a sensor (which can also be referred to as detector unit or magnetic sensing element) and/or through an underlying structure, whereby the combination of said external magnetic field with the magnetic field generated by said current allows said magnetic particles to move towards a predetermined location with respect to said sensor, measuring the magnetic field generated by said magnetic particles and relating this magnetic field to the presence and/or concentration of said magnetic particles.

Preferably, said external magnetic field is in-plane with respect to said surface, whereby the combination of said external in-plane magnetic field with the magnetic field generated by said current allows said magnetic particles to move towards the top and centre of each sensor.

More preferably, said external magnetic field is perpendicular with respect to said surface, whereby the combination of said external perpendicular magnetic field with the magnetic field generated by said current allows said magnetic particles to move towards one of the edges of each sensor.

Said solution containing said magnetic particles can comprise one or more additives suitable for inducing a repulsive force between said magnetic particles and said surface of the device. The movement of said magnetic particles in said solution, on said surface, is then facilitated. Said repulsive interaction can consist mostly (i.e. more than 50%) of an electrostatic interaction, which can be induced by the presence of charges of equal sign on said surface and on said magnetic particles.

Said repulsive interaction can be generated by the adsorption onto said magnetic particles and/or onto said surface of anionic or cationic surfactant(s) (which is/are specific example(s) of said additive(s)) added to said solution.

Said additive(s) may also be selected to induce a change in the pH and/or ionic strength, whereby said repulsive interaction is generated. More particularly, said additive(s) is/are selected for providing a pH larger than 9 and/or a ionic strength between 1 mM and 1 M.

Preferably, in a method of the invention, the absolute values of the induced electrostatic potentials between said solution and said device surface and between said solution and each magnetic particle are respectively larger than 5 mV.

A method according to the invention can be used for detecting and/or quantifying an analyte, said analyte being labelled by said magnetic particles.

Said analyte can also be referred to as a ligand. Said analyte can be any molecule(s), in particular any biomolecule (e.g. sugar(s), protein(s), antigen(s), antibody (-ies), enzyme(s), oligonucleotide(s), DNA, RNA, hormones, neurotransmitters, etc.), or any combination thereof. Said analyte can also be a cell, a bacterium, a virus or any biological entity. Preferably, said analyte is from one or more biospecimens.

Said analyte can be labelled by binding directly with said magnetic particles through groups present on the surface of said magnetic particles and groups present on/in said analyte, or indirectly through one or more molecules, preferably biomolecules (e.g. biotin, avidin, strepavidin, protein A, protein G, receptor(s), antibody (-ies), enzyme(s), etc.), that are attached to said magnetic particles.

In a method of the invention, the presence and/or amount of said analyte (or ligand) can be correlated to the presence and/or number of said magnetic particles.

Said step of measuring the magnetic field generated by said magnetic particles and relating this magnetic field to their presence and/or concentration, can be performed while said analyte is bound to said magnetic particles. It can also be performed separately from said analyte, after the magnetic particles have reacted selectively (i.e. have been bound selectively) with said analyte, e.g. through one or more chemical groups or one or more receptors, and have been retrieved.

In a method of the invention, said analyte can be added to said solution containing said magnetic particles before, during or after said solution is provided to said surface of said sensor device. Said analyte may thus be provided to said surface together with or separately from said magnetic particles.

A method according to the invention can further comprise the step of immobilizing on said surface of the device one or more receptor(s) susceptible of binding, preferably selectively, with said analyte.

Said receptor(s) can be any molecular structure susceptible of binding, preferably selectively, with said analyte (or ligand).

In a method according to the invention, said analyte can be brought on said surface separately from or together with said magnetic particles. Said analyte and/or said magnetic particles can be prevented from binding with said receptor(s) by adding one or more additives suitable for preventing and/or breaking the bond(s), or by physical means. By applying said current through said sensor(s), said magnetic particles move towards said predetermined location, where the complex analyte—receptor(s)—magnetic particles are then allowed to form.

Alternatively, in a method according to the invention, said analyte can be brought on said surface separately from or together with said magnetic particles, and be allowed to bind with said receptor(s).

At that stage, an intermediary step of measuring the magnetic field generated by said magnetic particles can be performed.

Then, before applying said current, a further step is performed of breaking the molecular bond(s) between said analyte and said receptor by adding one or more suitable additives or by physical means.

A method of the invention may then further comprise, during or after the step of applying said current and before the step of measuring the magnetic field, the step of allowing the bond(s) to form between said analyte and said receptor.

Nevertheless, since the selective binding has already occurred, it is preferred to apply said current without the step of allowing the bond(s) to form (for instance by adding one or more suitable additives or by physical means), for moving said magnetic particles towards said predetermined location for measurement.

Said additive(s) suitable for preventing or breaking the bond(s) between said analyte (or ligand) and said receptor(s) can be the same as the additive(s) selected for generating a repulsive interaction between said device surface and said magnetic particles.

Preferably, said additive(s) is/are selected for changing the pH and/or ionic strength.

In a method of the invention, said device surface can be (in some cases should be) washed between some of the binding steps. Preferably washing steps are performed after each binding step.

Said magnetic particles are any particles suitable for detection or diagnostic applications that are magnetically susceptible and capable of producing magnetic fields when magnetized by an external magnetic field and/or with a magnetic field generated by said current. Materials for said magnetic particles include, but are not limited to ferromagnetic, ferrimagnetic, paramagnetic, or superparamagnetic materials.

These materials can be used as such or can be present in an inert/active material, which is not sensitive to magnetic field as such, comprising the magnetic particle.

Said magnetic particles are preferably magnetic beads, but any shape particles can be used.

The diameter of said magnetic particles is preferably comprised between about 1 nm and about 50 μm. They are not necessarily uniform in size.

Another object of the invention relates to a sensor apparatus for carrying out a method according to the invention.

A sensor apparatus of the invention can comprise:
- a substrate comprising an active surface upon which magnetic particles, in a solution, are deposited for measurement of their magnetic field,
- one or more sensors (also referred to as detector units or magnetic sensing elements),
- means for providing an external magnetic field to said magnetic particles, preferably in-plane, and more preferably perpendicular with regard to said surface,
- means for applying a current through said sensor(s) or through a structure underlying said sensor(s).

In a sensor apparatus according to the invention, said structure underlying said sensor(s) can carry said current independently.

Preferably, said structure underlying said sensor(s) has the same size as said sensor(s) and/or is aligned to said sensor(s).

A sensor apparatus according to the invention can further comprise a solution containing magnetic particles and one or more additives suitable for providing a repulsive force between said magnetic particles and said surface. Said repulsive interaction can consist mostly (i.e. more than 50%) of an electrostatic interaction.

Said electrostatic interaction can be induced by the presence of charges of equal sign on said surface and on said magnetic particles, which can be generated by the adsorption onto said particles and/or onto said surface of anionic or cationic surfactant added to said solution.

Preferably, said additive(s) is/are suitable for inducing a change in the pH and/or ionic strength whereby said repulsive interaction is generated.

Preferably, in a sensor apparatus of the invention, the absolute values of the induced electrostatic potentials between said solution and said surface and between said solution and each magnetic particle are respectively larger than 5 mV.

In one embodiment, a sensor apparatus of the invention further comprises a receptor immobilized on said surface, susceptible of binding with an analyte (which is to be labelled by said magnetic particles) contained in or brought to said solution.

A sensor apparatus according to the invention can further comprise one or more additive(s) suitable for allowing dissociation between said analyte and said receptor and/or between said analyte and said magnetic particles.

A sensor apparatus according to the invention can be adapted from a Giant Magneto Resistance (GMR) sensor device, from an Anisotropic Magneto-Resistance (AMR) sensor, from a Tunnel Magneto-Resistance (TMR) sensor, an preferably from a spin-valve sensor, by providing means for applying a current through the sensor(s) of said devices, and/or by providing means for applying a current through one or more underlying structures, preferably aligned to said sensor(s).

Another object of the present invention relates to a solution (also referred to as composition of the invention) to be used in a method and/or a sensor apparatus according to the invention, which can be any liquid mixture comprising one or more additives suitable for providing a repulsive force between said magnetic particles and said surface of the device (or apparatus). The movement of said magnetic particles in said solution, on top of said surface, is thus facilitated.

Said composition is preferably compatible with an analyte and/or a receptor originating from biospecimens.

Said additive(s) can be anionic or cationic surfactant(s) adsorbed onto said magnetic particles and/or onto said surface, whereby generating said repulsive interaction.

Said additive(s) may also be selected to induce a change in the pH and/or ionic strength, whereby said repulsive interaction is generated. More particularly, said additive(s) is/are selected for providing a pH larger than 9 and/or a ionic strength between 1 mM and 1 M.

SHORT DESCRIPTION OF THE DRAWINGS

FIG. 1 represents a simulated output signal from the sensor of the present invention. FIG. 1(a) represents a simulated output signal for an external magnetic field, with a perpendicular orientation with regard to the sensor surface, applied onto the magnetic particle. FIG. 1(b) represents a simulated output signal for an external magnetic field, with an in-plane orientation with regard to the sensor surface, applied onto the magnetic particle.

Figure 2:
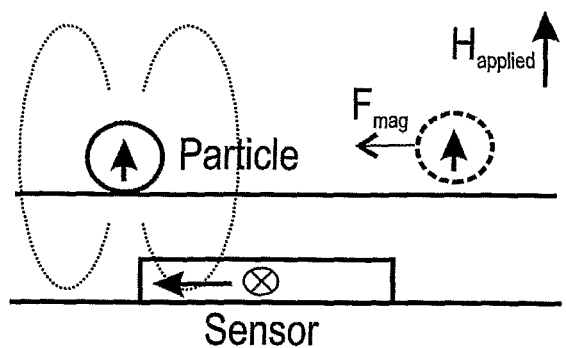

FIG. 2 represents the position of magnetic particles towards the edge of the sensor. The combination of the magnetic field generated by the current applied to the sensor with the external magnetic field (perpendicular with regard to the surface) provided to the magnetic particle, creates a magnetic field gradient that allows the particle to move towards one of the edges of the sensor.

FIG. 3 (a) corresponds to the lay-out of a prior art sensing area. FIGS. 3 (b) and (c) are possible means for applying a current through sensors in an apparatus according to the invention. With a sensing area of FIG. 3(b), the effective sensing area decreases in comparison with FIG. 3(a), but the change in resistance as a result of the magnetic field of the particles remains comparable to the apparatus described in FIG. 3(a) decreases and the current is more efficiently controlled. With a sensing area of FIG. 3(c), the effective sensing area is not reduced and the sensor measures average particle distribution, which allows to correct for non-uniform immobilization of magnetic particles.

Figure 4A:
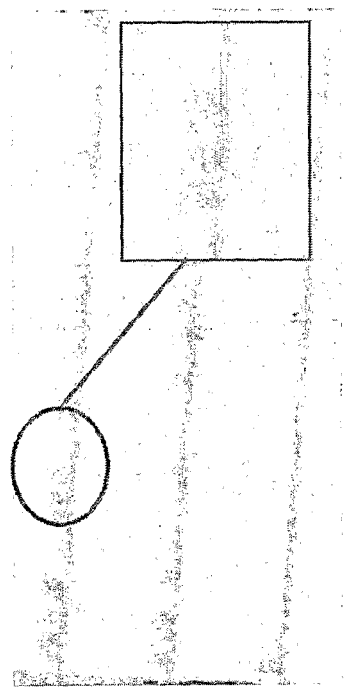
Figure 4B:
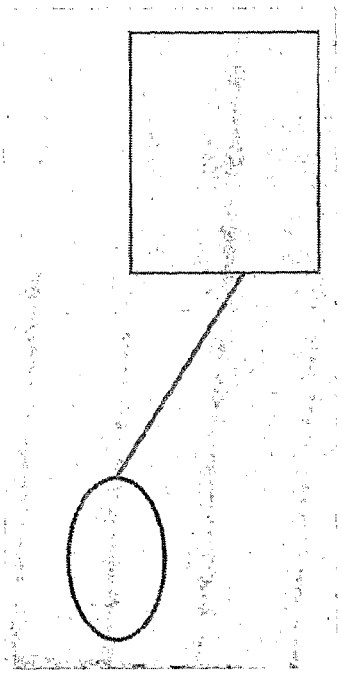

FIG. 4(a) shows the location, i.e. the top and centre of each sensor, where the magnetic particles have been positioned with no external magnetic field applied or alternatively in case an in-plane magnetic field is applied, after applying a current through the sensors. FIG. 4(b) shows the location, i.e. the top and one single edge of each sensor, where the magnetic particles have been positioned after applying a current through the sensors in combination with an external magnetic field perpendicular with regard to the surface.

Figure 5B:
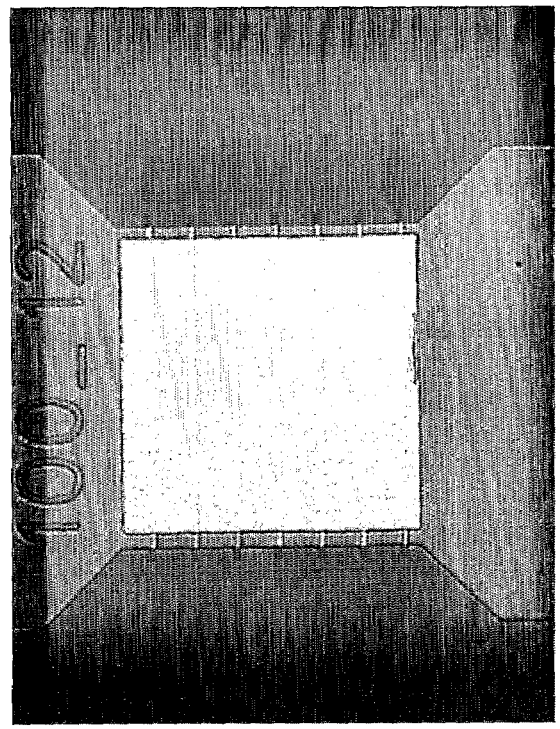
Figure 5A:
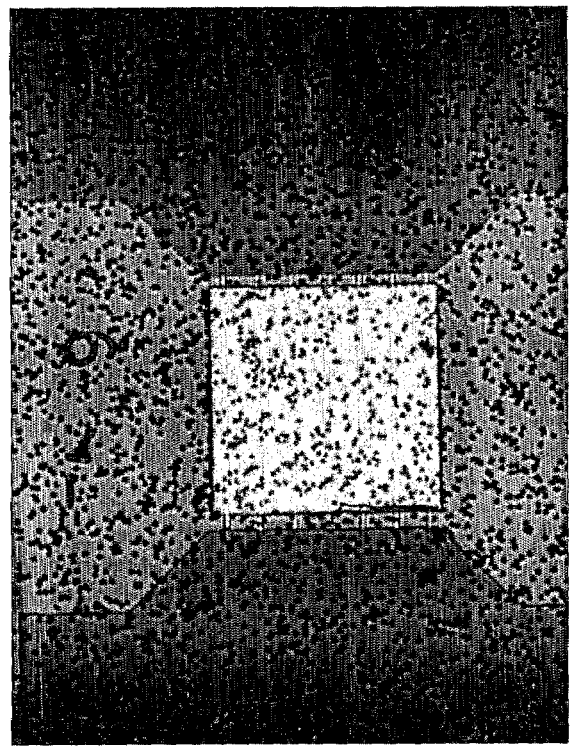
Figure 5C:
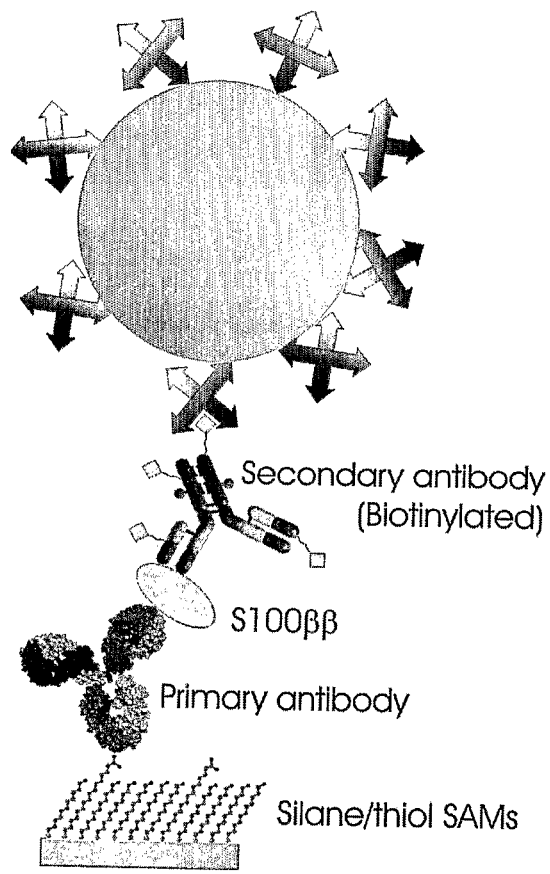

FIG. 5 (a) shows a microscopic image of the sensor surface and surrounding area after the binding of magnetic particles via a sandwich assay as depicted in FIG. 5 (c). FIG. 5 (b) shows a microscopic image of the sensor surface and surrounding area for a control experiment in which the ligand (i.e. the stroke marker S100ββ, see FIG. 5 (c)) was not added, hence no magnetic particle binding was observed. FIG. 5 (c) represents a schematic representation of the sandwich assay applied for these experiments. Onto the sensor surface a linking layer (i.e. a Self-Assembled Monolayer of thiols/silanes) is applied, followed by: the immobilisation of a receptor (i.e. a primary antibody), the binding of the ligand (i.e. the stroke marker S100ββ), the binding of a biotinylated secondary antibody, and, the binding of streptavidin-coated magnetic particles (i.e. 1 μm sizes particles, such as MyOne® particles of Dynal).

Figure 6A:
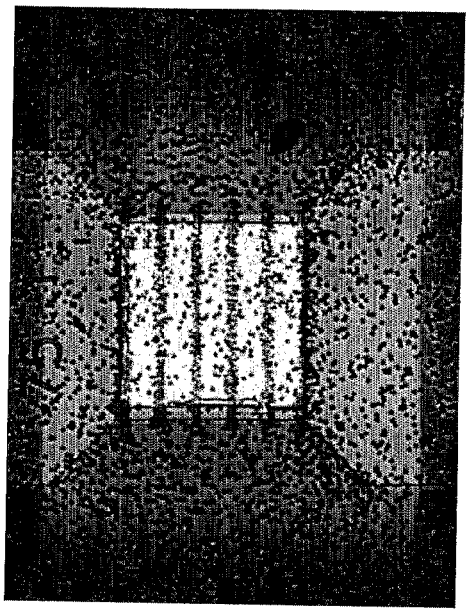
Figure 6B:
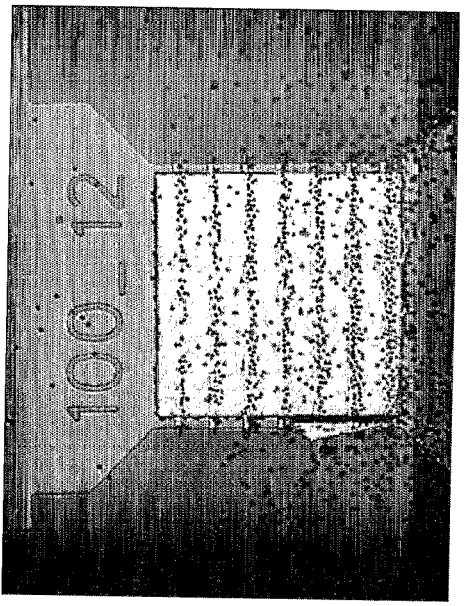
Figure 6C:
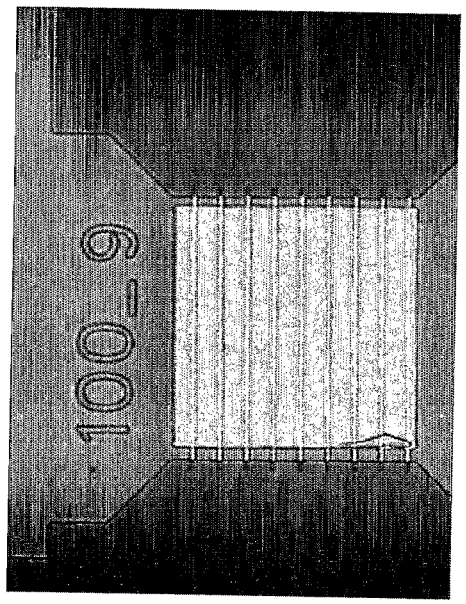

FIG. 6 (a) shows a microscopic image of the sensor surface and surrounding area after building up the sandwich assay of FIG. 5 (c) wherein the magnetic particles are submitted to an in-plane external field (with regard to the surface) combined with a magnetic field generated by the current applied (through the sensors). Following this method, the particles are located on the top and centre of each sensor. FIG. 6 (b) shows a microscopic image of the sensor surface and surrounding area after building up the sandwich assay of FIG. 5 (c) wherein the magnetic particles are submitted to a perpendicular external field (with regard to the surface) combined with a magnetic field generated by the current applied (through the sensors). Following this method, the particles are located on the top and one of the edges of each sensor. FIG. 6(c) shows a microscopic image of the sensor surface and surrounding area for a control experiment in which the ligand (i.e. the stroke marker S100ββ, see FIG. 5 (c)) was not added. Hence no magnetic particle binding was observed after submitting the magnetic particles to any external field (with regard to the surface) combined with a magnetic field generated by the current applied (through the sensors).

DETAILED DESCRIPTION OF THE INVENTION

In a first aspect of the present invention a method is disclosed for (re-)enabling transport by means of a magnetic field gradient transport mechanism of magnetic beads comprising a ligand in a solution on top of a surface comprising a receptor bound with the ligand, comprising the step of changing the properties of the solution such that dissociation occurs between the ligand and the receptor, and such that a sufficient repulsive interaction is created between the surface and the bead to allow transport of the bead.

In certain embodiments a repulsive interaction that maintains mobility is dominated by an electrostatic interaction.

In other embodiments according to the present invention wherein the repulsive interaction comprises also a steric or structural interaction.

It is moreover possible that only electrostatic interactions play a significant role or only steric or structural interactions play a significant role.

In preferred embodiments the electrostatic interaction is at least partially induced by the presence of charges of equal sign on the device surface and/or the bead surface.

In certain embodiments the repulsive interaction is at least partially created by the adsorption of anionic or cationic surfactant onto at least one of the bead surface or device surface, the surfactant added to the solution.

In preferred embodiments of the present invention, the step of changing the properties of the solution comprises, for a given surface and bead type, changing the pH and/or ionic strength appropriately in order to generate the repulsive interaction.

This can for instance be done by adding organic or inorganic acids and bases.

In preferred embodiment of the present invention the absolute values of the induced electrostatic potentials between the bulk solution and the surface and the bead surface respectively is larger than 5 mV.

In preferred embodiments the ligands and/or receptors are biospecimen.

In certain embodiments of the present invention the pH and ionic strength are selected to allow dissociation of the ligand and receptor.

The pH and ionic strength can be further chosen in order to change the functionality of the ligand and/or the receptor.

In another aspect of the present invention a method for determining an optimal pH and ionic strength of a solution is disclosed for a given set of bead, device surface, and a biospecimen ligand and receptor, such that magnetic transport is allowed on top of the surface in the solution, comprising the steps of:
  defining a maximum allowable pH value for the biospecimen ligand in order to allow the biospecimen ligand to be released from a receptor;
  defining an allowable ionic strength range for the biospecimen ligand and/or receptor;
  provide a solution with the maximum pH value and within the ionic strength range wherein magnetic transport is possible.

In certain preferred embodiments of this aspect of the present invention the solution comprises at least one surfactant.

In certain preferred embodiments of this aspect of the present invention the dissociation of the ligand and receptor in a solution may be assisted by physical means, such as heating the solution, flowing the solution over the device or stirring the solution on top of the device, applying ultrasonic forces, etc.

In yet another aspect of the present invention, a sensor apparatus is described, comprising:
  Means for controlled magnetic transport of magnetic beads on top of a surface comprising a receptor;
  A solution comprising magnetic beads comprising a ligand;
    wherein the properties of the solution are selected to allow binding or dissociation of the ligand and the receptor and provide a repulsive force between the beads and the surface, such that magnetic transport of the beads is possible.

In preferred embodiments the repulsive interaction is dominated by an electrostatic interaction. The repulsive interaction can also comprise mainly a steric or structural interaction.

It is moreover possible that only electrostatic interactions play a significant role or only steric or structural interactions play a significant role. In certain embodiments the electrostatic interaction is at least partially induced by the presence of charges of equal sign on the surface and/or the bead surface.

The solution can comprise additives such that the repulsive interaction is at least partially created by the adsorption of additives onto at least one of the bead surface or device surface.

In preferred embodiments an apparatus is disclosed wherein the pH of the solution is larger than 9. In preferred embodiment the ligands and/or receptors are biospecimen.

The ionic strength of the solution is preferably between 1 mM and 1 M.

In advantageous embodiments the absolute value of the induced electrostatic potentials between the bulk solution and the surface and the bead surface respectively are both larger than 5 mV.

In preferred embodiments the magnetic transport is performed with magnetic field strengths and magnetic field gradients that generate forces. Typical such forces are from about 0.05 pN to about 5 pN for in-plane transport and from 0.5 to 30 pN towards the surface, depending on the magnetic field gradient generating structure, the position of the particle and the current in the current carrying structure which is used to generate the magnetic field(s).

In another aspect of the present invention a method for measuring magnetic beads is disclosed wherein magnetic beads are transported towards a measurement location in the neighbourhood of said detection unit. It should be brought to the area from where the beads would generate a significant signal in the detection unit such that measurement is possible.

Advantageously the beads are transported such that they are substantially centred above the edges of the detector unit (e.g. a magnetoresistive sensor (MR), e.g. a GMR sensor (Giant MR), a spin valve sensor, an anisotropic MR (magnetic sensor).

In another aspect of the present invention a method for detection of biospecimen attached to magnetic beads in a solution is disclosed, comprising the steps of:

Allowing biospecimen to get bound to a receptor immobilized on the surface by which molecular bonds are formed;

Breaking the molecular bonds by means of adding additives to the biospecimen suspension, and/or by physical means (such as heating, flowing or stirring the solution on top of the device, by applying ultrasonic forces, etc.);

Transporting the magnetic beads to the area in which the magnetic sensor is situated. It should be brought to the area from where the beads would generate a significant signal in the detection unit such that measurement is possible. In advantageous embodiments another step can be performed of bringing the beads further on a measurement location where they generate the largest signal in a detection unit;

Measuring the magnetic field generated by the magnetic beads by means of the detection unit.

Advantageously the measurement location is substantially centred above the edges of the detector unit.

The present invention builds on the idea of a dynamic sensor, to release and reposition immobilised particles by regenerating the biomolecular bond. For this, one needs to be able to transport magnetic particles and break biomolecular bonds in one step.

However, in some applications (such as breaking biomolecular bonds), it is usually necessary to resuspend these particles using a solution with specific pH and ionic strength. Although magnetic particles can be resuspended by breaking recognition events, e.g. biomolecular bonds, it can be experimentally shown that these particles not always move. It can be shown that e.g. streptavidin-coated particles no longer move in a pH 2, 10 mM solution for typical magnetic forces on the beads and a $SiO_2$ surface. Typical forces are from about 0.05 pN to about 5 pN for in-plane transport and from 0.5 to 30 pN towards the surface, depending on the magnetic field gradient generating structure, the position of the particle and the current in the current carrying structure which is used to generate the magnetic field(s).

It is believed that this is due to electrostatic interactions events which is believed to be predictable by DLVO theory.

The invention therefore relates to methods for movement of magnetic particles in solutions other than pure water, e.g. solutions with pH values in the order of 2-12 and different from 7 in case the ionic strength is not 1E-7 M, and ionic strengths e.g. 1 mM-10 mM. (e.g. 10 mM NaOH gives pH 12, ionic strength of 10E-2). In these solutions, magnetic forces are not always the dominant forces acting on the particle and depending on the conditions particles can be immobilised or trapped onto the surface. It is believed that electrostatic and van der Waals interactions are at least partly responsible for these effects. The electrostatic force depends on the total charge of both the particle and device surface, which is a function of the pH, and the ionic content and strength, which screens these charges.

It is believed that also other forces are acting on the magnetic beads or particles as for instance steric or structural forces (e.g. hydrophobicity, conformation and allostery).

One needs thus to understand the forces acting on the magnetic beads to stabilise the system and make manipulation of magnetic particles in solution other than water still possible.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The active substrate of the magnetic sensor can consist for instance of a metal (e.g. gold) surface or an oxide surface. These surfaces can be modified with, amongst others, self-assembled monolayers (SAMs) of thiols or silanes as coupling layers. These SAMs can be homogeneous or a mixture of different molecules, presenting different end-groups especially designed towards reduction of non-specific binding of the analyte and towards good characteristics for coupling the receptor molecules. Different protein receptors, e.g. conventional antibodies, chemically modified conventionally antibodies, recombinant scFv's (Single Chain F Variable), recombinant VHH camel antibodies, aptamers (or any other biomolecule known by the skilled person to be usable as a receptor for protein detection), can be attached, preferably covalently, to the coupling layer by the usage of various coupling chemistries, followed by one or more blocking step(s) of the complete sensor surface. The sensor platform is now ready to perform different types of assays, i.e. inhibition assays, competition assays, displacement assays and ELISA-like sandwich assays, all using magnetic particles as label in the final binding step, or in different steps of this binding cascade. All these assays are mostly based on biomolecular interactions and most assays make use of secondary antibodies. Modification of the secondary antibodies and conjugation of the magnetic particles with the corresponding biospecies is in most cases necessary. Commonly used receptors/ligands are, but are not limited to biotin modified antibodies/streptavidin modified magnetic particles, digoxigen modified antibodies/Anti-digoxigen modified magnetic particles, not modified antibodies/proteinA or proteinG modified magnetic particles, 6His labelled antibodies/Ni-NTA modified magnetic particles, etc. The device surface is washed between some binding steps and preferably each binding step of the assay. To allow quantitative detection of the analyte, the biomolecular interactions need to be efficiently regenerated by the use of typical regeneration buffers, which are known by the skilled person in the field. These buffers will break one or more biomolecular bonds in the assay and have to be compatible with the release and repositioning of the magnetic particles sensor principle, which is based on the movement of magnetic particles.

The substrate, coupling layer, type of assay, type of receptor/ligand interaction and regeneration are similar are based on similar principles, known by the skilled person in the field, for the detection of nucleic acids and whole cells.

The present invention concerns a method for controlled manipulation of magnetically labelled biomolecules, in close proximity to a surface, in a solution with a given pH and ionic strength given that system is stabilised by repulsive forces. The solution used may depend on the type of application:
- for stabilisation of biological species during transport
- for regeneration of biomolecular bonds.

In these solutions, charging of the particle surface and device surface and screening of these charges may occur, causing particles to adhere to the device surface. To avoid this, repulsive forces are required to stabilise the system. These repulsive forces may be either:
- Electrostatic forces: as successfully explained by DLVO theory. This can be accomplished by either adjusting the solution itself (e.g. use pH 11 instead of pH 2 to regenerate bonds) or, when adjustment of the solution is not possible, by adjusting the surface properties of the substrate or particle itself e.g. using dedicated surface chemistry, or via the proper choice of the substrate and particle surface material.
- Non-DLVO forces, such as steric interactions.
- Magnetic forces: use of upward oriented force.
- Other electrostatic forces than described above by applying voltage with electrode)

Given the dipole field generated by magnetic particles with an external field perpendicular to the surface, one can calculate that the signal will be maximised when only 50% of the particle covers one track MR sensor, which can be a single rectangular stripe, or serpentine shaped structure as shown in BARC III ("Design and Performance of GMR sensors for the detection of magnetic microbeads in biosensors", J. C. Rife, M. M. Miller, P. E. Sheehan, C. R. Tamanaha, M. Tondra and L. J. Whitman, "Sensors and Actuators A", 107, 2003, p 209-218). This can be achieved by releasing the particles, applying an external magnetic field with a perpendicular-to-plane orientation and by putting a (small) current trough the sensor (experimentally verified) or through a structure underlying the sensor, which can independently carry a current and which can be for instance of the same size of the sensor and aligned to the sensor or a similar structure having the same effect. When the particle is in the vicinity of the sensor, it will be attracted towards the edge of the sensor, maximising the signal (FIG. 2). Particles on opposing edges of a detector unit may induce complementary signals in the unit such that the total signal may be reduced. Therefore it is advantageous to apply an external magnetic field perpendicular to the surface which will not be sensed by the sensor, but which will remove particles at one of the opposing edges (and possibly moves those beads to the other opposing edge). This way the signal strength will again be increased.

Magnetic particles coated with streptavidin can be transported when dispersed in solution with pH 12, but stop moving when the pH drops below pH4. When ionic strength is lowered, particle mobility increases.

Magnetic particles with acrylate surface move little or not at any pH value smaller then 6 and ionic strength of 10 mM. Experimental details:
15' UV Ozone clean
I=75 mA
Surface $SiO_2$ sputtered
Particle conc.: 1/300 ml
W=water like movement
L=low force movement (on conductor)
H=high force movement (between 2 conductors)
N=no movement
+, −, 0=surface or particle charge
First column for each pH value indicates surface charge sign, second columns indicates particle surface sign.

| | | Micromer-M uncoated (acrylate) | | | | | | | | |
|---|---|---|---|---|---|---|---|---|---|---|
| | | pH 2 | | pH 4 | | pH 6.3 | | pH 8.2 | | pH 10 |
| 1 mM | N | N | | N | | N | | L | W | L | W | W | W |
| 10 mM | N, 0 | N, + | N, − | N, + | L, −− | H, 0 | L, −− | H, − | L, −− | L, −− |
| 100 mM | | | N | N | N | N | H | H | H | H |

| | | Micromer-M streptavidin coated | | | | | | | | |
|---|---|---|---|---|---|---|---|---|---|---|
| | | pH 2 | | pH 4 | | pH 6.3 | | pH 8.2 | | pH 10 |
| 1 mM | N | N | W | W | W | W | W | W | W | W |
| 10 mM | N, 0 | N, + | L, − | L, − | L, −− | W, −− | L, −− | W, −− | L, −− | W, −− |
| 100 mM | | | H | L | H | L | L | L | L | W |

The present invention thus provides a magnetic particle detector capable of breaking bonds and subsequently repositioning the particles to a better place so that a higher detection signal is obtained. An enhancing effect obtained by moving particles towards the sensor is only advantageous for low analyte/particle concentrations. If the concentration of particles is too high, particles will start to form clusters. This will make it more difficult to get a quantitative result from the sensor. The skilled person can easily determine a suitable particle concentration to obtain optimal results.

FIG. 1 shows a simulated output signal from the sensor when a magnetic particle with (a) an out-of-plane (perpendicular) or (b) in-plane magnetisation is moved along the sensitive axis of the sensor. Sensor width is 2 micron, signal is maximised when the centre of the particle (2 micron diameter) is located above the edge of the sensor. Thus, 50% of the particle is covering the sensor. In case of an out-of-plane component, the signal is maximised when the particle is completely covering the sensor (centre of particle and centre of sensor are at the same position.

FIG. 2 draws the repositioning of magnetic particles towards the edge of the sensor. Only about 50% of the particle will cover the sensor, maximising in this way the signal measured by the sensor.

As described before, magnetic particle detectors sense random magnetic fields coming from magnetic particles positioned at different locations from the sensor. This lowers the average signal contribution for one magnetic particle. In order to solve this problem, one needs to be able to break biomolecular bond and transport the magnetic particles in this solution. In this way, the random contribution of each particle is removed: all particles contribute to the signal in the same amount since their distance to the sensor is constant. Further, the signal from 1 particle is maximised by both placing the particle at the optimal position and by adjusting the sensor geometry for optimal performance (extra degree of freedom).

Breaking biomolecular bonds and ensuring the continued interaction (electrostatic, etc.) of the bead with the substrate, requires transport of particles in specific buffers for proteins, DNA as well as whole cells.

The invention claimed is:

1. A method of measuring the presence and/or concentration of magnetic particles comprising:
   providing a surface of a sensor device with a solution comprising magnetic particles,
   subjecting the magnetic particles to an external magnetic field,
   applying a current through a sensor and/or through an underlying structure, wherein the combination of the external magnetic field with the magnetic field generated by the current creates a magnetic field gradient that allows the magnetic particles to move towards a predetermined location with respect to the sensor in a direction parallel to the surface of the sensor device, and
   measuring the magnetic field generated by the magnetic particles and relating this magnetic field to the presence and/or concentration of the magnetic particles,
   wherein the external magnetic field is in-plane with respect to the surface, wherein the combination of the external in-plane magnetic field with the magnetic field generated by the current allows the magnetic particles to move towards the top and center of the sensor.

2. The method according to claim 1, further comprising detecting and/or quantifying an analyte labelled by the magnetic particles.

3. The method according to claim 2, wherein the analyte is provided to the surface with or separately from the magnetic particles.

4. The method according to claim 2, wherein the analyte is directly or indirectly bound to the magnetic particles.

5. The method according to claim 2, wherein a receptor, susceptible of binding with the analyte, is immobilized on the surface.

6. The method according to claim 5, further comprising, before applying the current, preventing or breaking the molecular bond(s) between the analyte and the receptor by adding one or more suitable additives or by a physical mechanism.

7. The method according to claim 5, further comprising, during or after the applying of the current and before the measuring of the magnetic field, allowing the bond(s) to form between the analyte and the receptor.

8. The method according to claim 1, wherein the analyte is a molecule, a cell, a virus, or any biological entity.

9. The method according to claim 1, wherein the analyte and/or the receptor is/are from one or more bio-specimens.

10. The method according to claim 1, wherein one or more additives suitable for generating a repulsive interaction between the surface and the magnetic particles is/are added to the solution.

11. The method according to claim 10, wherein the repulsive interaction comprises mostly (more than 50%) an electrostatic interaction.

12. The method according to claim 11, wherein the electrostatic interaction is induced by the presence of charges of equal sign on the surface and on the magnetic particles.

13. The method according to claim 12, wherein the absolute values of the induced electrostatic potentials between the solution and the surface and between the solution and each magnetic bead are respectively larger than about 5 mV.

14. The method according to claim 10, wherein the repulsive interaction is created by the adsorption onto the particles and/or onto the surface of anionic or cationic surfactant added to the solution.

15. The method according to claim 10, wherein the additive (s) induces a change in the pH and/or ionic strength and generates the repulsive interaction.

16. The method according to claim 15, wherein the pH and/or ionic strength is/are selected to allow dissociation of the analyte and receptor.

17. The method according to claim 1, wherein the magnetic particles include magnetic beads wherein the beads are transported to a measurement location which is substantially centered above the edges of a detector unit and where the beads generate the largest signal in the detection unit.

18. The method according to claim 17, wherein the beads comprise a ligand in a solution on top of the surface of a measurement location comprising a receptor bound with the ligand, allowing the measurement of the presence and/or concentration of the ligands in a solution.

19. The method according to claim 17, wherein the receptors and/or ligands are biospecimens.

20. A method of measuring the presence and/or concentration of magnetic beads comprising a ligand in a solution on top of a surface comprising a receptor, comprising:
   allowing the ligand to bind to the receptor immobilized on the surface by which molecular bonds are formed;
   breaking the molecular bonds by adding additives to the solution;
   transporting the magnetic beads to the area in which a detector unit is located, and bringing the beads to a measurement location where they generate the largest signal in the detection unit;
   measuring the magnetic field generated by the magnetic beads by the detection unit and relating the magnetic field to the presence and/or concentration of the magnetic beads,
   wherein transporting the magnetic beads comprises subjecting the magnetic beads to an external magnetic field that is in-plane with respect to the surface.

21. The method according to claim 20, wherein the presence and/or concentration of magnetic beads is measured by allowing the ligand to bind to the receptor immobilized on the surface on top of a detection unit by which molecular bonds are formed, followed by the second, third and fourth steps of claim 20 in order to increase the signal in the detection unit.

22. The method according to claim 20, the method further comprising changing the properties of the solution such that dissociation occurs between the ligand and the receptor, and such that a sufficient repulsive interaction is created between the surface and the bead to allow the transporting of the beads by a magnetic field gradient transport mechanism.

23. The method according to claim 22, wherein the repulsive interaction is dominated by an electrostatic interaction.

24. The method according to claim 23, wherein the electrostatic interaction is induced by the presence of charges of equal sign on the surface and/or the bead surface.

25. The method according to claim 24, wherein the absolute values of the induced electrostatic potentials between the bulk solution and the surface and the bead surface respectively are larger than about 5 mV.

26. The method according to claim 22, wherein the repulsive interaction is created by the adsorption of anionic or cationic surfactant onto at least one of the bead surface or surface, the surfactant added to the solution.

27. The method according to claim 22, wherein the changing of the properties of the solution comprises, for a given surface and bead type, changing the pH and/or ionic strength appropriately in order to generate the repulsive interaction.

28. The method according to claim 22, wherein the pH and ionic strength are selected to allow dissociation of the ligand and receptor.

29. The method according to claim 22, wherein the receptors and/or ligands are biospecimen.

* * * * *